United States Patent [19]
Chang

[11] Patent Number: 5,693,164
[45] Date of Patent: Dec. 2, 1997

[54] METHOD OF MAKING BREAST ENHANCERS

[75] Inventor: Jasper Chang, Walnut, Calif.

[73] Assignee: Bragel International, Inc., Walnut, Calif.

[21] Appl. No.: 597,668

[22] Filed: Feb. 7, 1996

[51] Int. Cl.$^6$ .................................................. B32B 31/20
[52] U.S. Cl. .......................... 156/152; 156/221; 156/285; 156/290; 156/308.4; 264/266; 264/267; 264/510; 264/511
[58] Field of Search .................... 264/511, 510, 264/465, 266, 267; 156/290, 308.4, 245, 152, 285, 221

[56] References Cited

U.S. PATENT DOCUMENTS

| | | | |
|---|---|---|---|
| 4,247,351 | 1/1981 | Rechenberg | 156/221 |
| 4,249,975 | 2/1981 | Rechenberg | 156/245 |
| 4,270,965 | 6/1981 | Torterotot et al. | 156/308.4 |
| 4,447,373 | 5/1984 | Chappell et al. | 264/4 |
| 4,701,230 | 10/1987 | Loi | 156/145 |
| 5,035,758 | 7/1991 | Degler et al. | 156/61 |
| 5,340,352 | 8/1994 | Nakanishi et al. | 450/57 |
| 5,500,067 | 3/1996 | Jenkner | 156/245 |

*Primary Examiner*—Jan H. Silbaugh
*Assistant Examiner*—Mark Eashoo
*Attorney, Agent, or Firm*—Christie, Parker & Hale, LLP

[57] ABSTRACT

An improved method for making a breast enhancer comprises placing a first and second film of thermoplastic material adjacent one another and forming a temporary adhesion seal therebetween. The temporary seal is in the form of a band that defines a parameter of a bag formed between the two films. A sufficient volume of liquid silicone composition to form the breast enhancer is introduced into the bag, and the air-bubble free filled bag is placed between a top mold and a bottom mold. The top and bottom molds are compressively engaged to encase the filled bag within a mold cavity formed between the mold surfaces. At least a portion of the sealed band is disposed within the mold cavity, and at least a portion of the band is compressed between a seal surface of the top mold and a rim of the bottom mold. The temporary seal is opened to allow the liquid silicone composition to migrate between the films and fill the mold cavity. The liquid silicone composition is cured and a weld is formed between film portions positioned between the rim and seal surface. The top mold is withdrawn from the bottom mold, the breast enhancer is removed from the bottom mold, excess edges of the films are trimmed off, and the breast enhancer is ready for packaging and shipping.

28 Claims, 4 Drawing Sheets

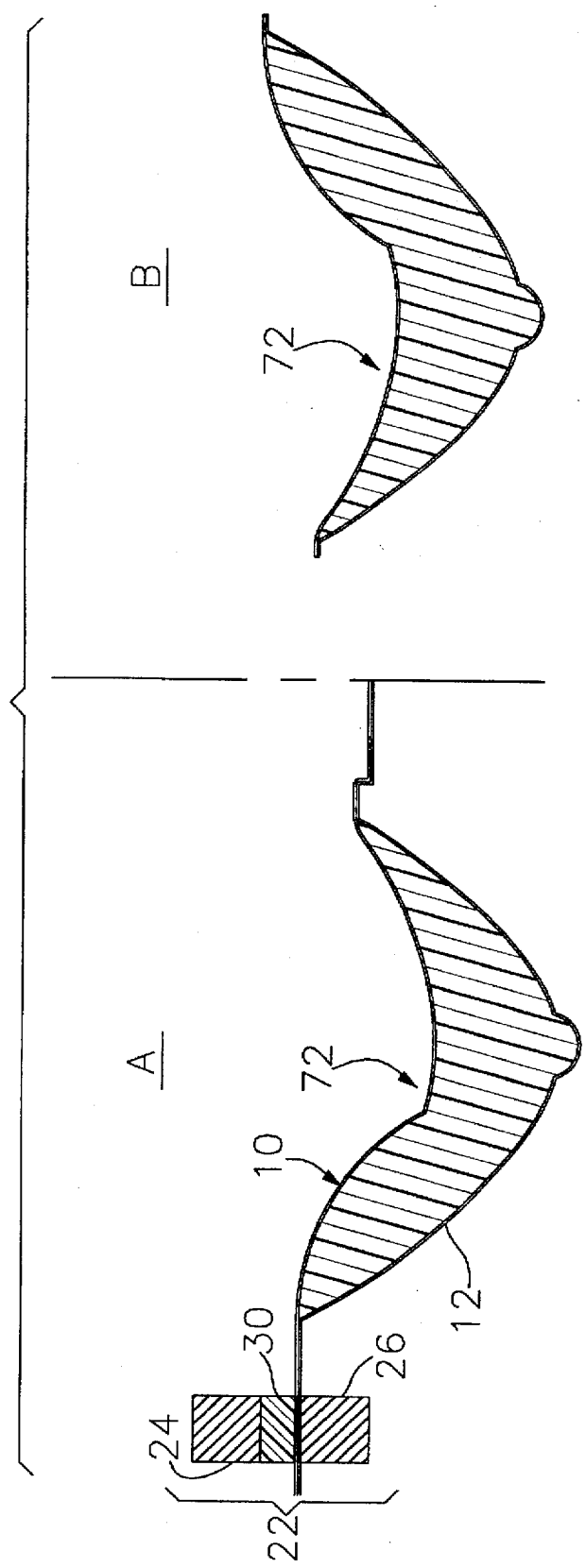

METHOD OF MAKING BREAST ENHANCERS

FIELD OF THE INVENTION

This invention relates to an improved method of making molded articles from silicone gel and, more particularly, to an improved method of making a female breast enhancer or bra pad made from silicone gel.

BACKGROUND OF THE INVENTION

Women who, for whatever reason, are not satisfied with the size of their own breasts and desire larger, more shapely breasts must select among two alternative methods for enhancing their breast size, by either using rudimentary externally worn articles, such as foam pads and the like, or by undergoing a surgical operation to be fitted with a breast implant. Opting for use of a surgical breast implant carries with it the danger inherent in any surgical operation and can be quite expensive. In addition to the dangers inherent with the surgical operation is the potential health dangers that may be associated with using a particular type of breast implant, namely, the silicone breast implant. Accordingly, women wishing to enhance their physical appearance in a non-permanent and health-risk free manner opt to use one of the many types of externally worn articles.

A key feature of such externally worn article is that it look and feel natural so as to complement and not detract from the existing female breast that it is used to enhance. Accordingly, a popular type of breast enhancer is one comprising a silicone gel material that is completely encased by a plastic film. The advantage of this type of breast enhancer is that it both looks like a natural human breast when worn and feels natural to the user, thus enhancing the self image and confidence of the user. Other breast enhancers, such as foam pads or the like, do not afford the user these important qualities but, rather, look unnatural and feel foreign, thereby diminishing any self image or amount of confidence a user may have in their physical appearance.

Related to silicone gel breast enhancers are silicone gel breast prostheses that, instead of enhancing the size of an existing female breast, are used to replace a female human breast that has been surgically removed. Methods for manufacturing silicone gel breast enhancers and breast protheses are known in the art. For example, U.S. Pat. No. 4,249,975 discloses a method for making artificial breasts using a two-component silicone rubber by introducing a sheath formed by welding two sheets of plastic material together into a lower female mold part. An upper male mold part is mounted onto the lower mold part by use of threaded studs connecting the two to form a hollow cavity therebetween containing the sheath. The two-component silicone rubber is charged into the sheath via a non-welded opening in the sheath. The mold is placed in an oven to cure the composition for between one and two hours, during such time the opening is welded shut by use of a punch in the mold. This method is both complicated and time consuming in that the upper and lower molds must be completely assembled and unassembled for the insertion and removal, respectively, of each sheath by tightening and untightening threaded couplings.

U.S. Pat. No. 4,701,230 discloses a method for manufacturing a breast prosthesis comprising a complicated multiple-step sequence of first forming a foam rubber member having both a convex and concave surface, shaping and molding an intermediate skin sheet upon the convex surface of the foam rubber member, positioning the intermediate skin sheet and foam rubber member within an outer skin sheet, shaping and positioning an inner skin sheet in contact with the concave surface of the foam member, sealing with the inner skin sheet the foam member and intermediate skin sheet combination and the outer skin sheet together about the peripheries thereof forming a combination having a cavity defined by the intermediate skin sheet and the outer skin sheet, filling the cavity with a liquid, and curing the liquid into a silicone gel. This method of manufacture results in the formation of a multi-component structure that is both complicated and time consuming to construct.

U.S. Pat. No. 5,035,758 discloses a method of making a breast prosthesis using a complicated multi-step process comprising stretching a film of thermoplastic material across an opening of a female mold and drawing the film onto the surface of the mold, removing the film from the mold, inserting an insert having a recessed portion into the female mold and placing the film into the female mold and onto the recess, filing the recess with a synthetic resin and curing the resin, filling the female mold with synthetic resin, stretching a second film of thermoplastic material over the opening of the female mold, welding the first and second films at overlapping edge portions, and removing the insert. A male mold is lowered into contact with the second film and into the female mold, heat is applied to the male and female mold halves to cure the resin, and the prosthesis is removed by lifting the male mold away from the female mold. Like the above-described methods, this method also requires a multitude of steps making the act of forming each breast prothesis a complicated and time consuming event.

Another method for forming a breast enhancer employs horizontally movable mold halves. Two thermoplastic polyurethane films are mounted in a frame which is placed between the mold halves, and the mold halves are closed against the films. A small channel is left at the top of the cavity between the male and female mold halves. Liquid silicone resin is injected between the films in the cavity through the channel at the top and allowed to sit for a time until any bubbles have risen through the channel. The proper amount of resin is determined by observing excess resin extruding from the channel. A slide in one half of the mold is pressed against the film on one of the mold halves, thereby closing the channel. The mold is then heated for curing the resin and finally sealing the films together adjacent the closed channel.

It is therefore, desirable, that an improved method for making a breast enhancer be developed that does not require a multitude of complicated and time consuming steps. It is also desired that the method employ conventional manufacturing techniques.

SUMMARY OF THE INVENTION

There is, therefore, provided in practice of this invention according to a presently preferred embodiment, an improved method for making a human breast enhancer comprising a volume of silicone gel encased between films or sheets of thermoplastic material. The breast enhancer is made by pressing a first and second thermoplastic film together and applying heat to the films to form a temporary adhesion seal therebetween. In a preferred embodiment, the temporary seal is in the form of a band that defines a parameter of a bag formed between the two films. The band parameter is approximately the outline of the breast enhancer.

The sealed band includes a non-sealed inlet channel that extends between the films through the band and into the bag. The sealed films and bag are placed between frame members of a holding frame assembly, and edges of the films are pulled or otherwise arranged to remove any wrinkles that may be present on the surfaces of the films. A sufficient volume of liquid silicone composition to form the breast enhancer is introduced into the bag via the inlet channel.

The frame apparatus holding the liquid silicone composition filled bag is placed between a top mold and a bottom mold. The top mold includes a floating member that has a convex external surface, and an outwardly extending seal surface positioned concentrically around the floating member. The bottom mold includes a concave surface and an outwardly extending rim that is positioned concentrically around the concave surface at a location that corresponds with the seal surface. In a preferred embodiment, the sealed band has an inside diameter that is less than an inside diameter of the outwardly extending rim, and an outside diameter that is greater than the inside diameter of the outwardly extending rim. The top and bottom molds are compressively engaged to encase the liquid silicone composition filled bag within a mold cavity formed between the convex and concave surfaces, and to compress the rim against the seal.

Heat is applied to at least one of the bottom mold and the floating member to cause the temporary adhesion seal to soften. The combination of heat and pressure exerted on the filled bag by the floating member causes the temporary seal to open and allows the liquid silicone composition to migrate between the films to fill the mold cavity. Further heat is applied to at least one of the top mold, the bottom mold, and the floating member to both form a weld between film portions positioned between the rim and seal to encase the liquid silicone composition, and to cure the liquid silicone composition to form as silicone gel. The heated molds are cooled, the top mold is withdrawn from the bottom mold, the breast enhancer is removed from the bottom mold, any excess edges of the films are trimmed off, and the breast enhancer is ready for packaging and shipping.

BRIEF DESCRIPTION OF THE DRAWINGS

These and other features and advantages of the present invention will become appreciated as the same becomes better understood with reference to the specification, claims and drawings wherein:

FIG. 4, Sections A and B, are split semi-schematic cross sectional views of breast enhancers formed according to principles of this invention, before and after trimming.

DETAILED DESCRIPTION

A human breast enhancer manufactured according to principles of this invention broadly comprises a body of silicone gel encased in a thin polyurethane sheath or pouch and having the shape of a human female breast. The enhancer, therefore, is configured having a convex portion facing outwardly away from the user and a concave portion at an opposite side of the enhancer that faces toward and against the body of the user.

Generally speaking, a breast enhancer is made according to principles of this invention by forming a temporarily sealed bag between two films of thermoplastic material, introducing a liquid silicone composition into the bag, placing the filled bag between top mold, floating member, and bottom mold, heating the molds to open the temporarily sealed portions of the thermoplastic films and to allow the liquid silicone composition to migrate between mold surfaces and form the desired shape of the breast enhancer, heating the molds to both cure the liquid silicone material and weld the films together to encase the cured silicone, and trimming the cured breast enhancer for shipping. Although the practice of this invention, as described and illustrated, is directed to the making of human breast enhancers, it is to be understood that the method of this invention can also be applied to make silicone gel filled devices other than breast enhancers.

Figure 1:
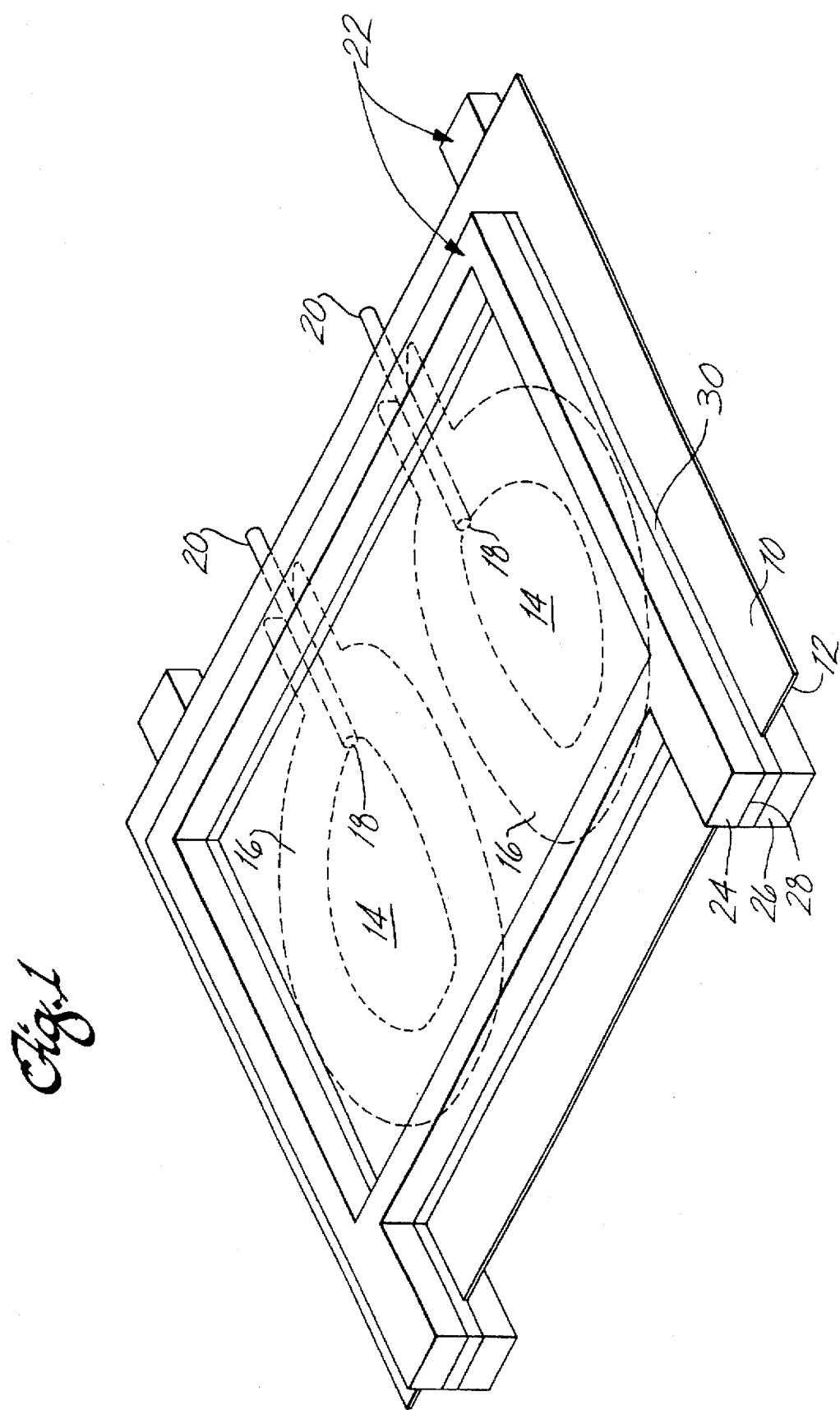
FIG. 1 is a semi-schematic perspective view of liquid silicone composition filled bags, constructed according to principles of this invention, formed between temporarily sealed films of thermoplastic material that are housed in a frame.

Referring to FIG. 1, a breast enhancer is formed by first placing two films or sheets 10 and 12 of thermoplastic film material side-by-side together. Suitable thermoplastic materials include polymeric materials such as polyurethane and the like. In a preferred embodiment, each film 10 and 12 is formed from a thin film of polyurethane having a thickness in the range of from about 20 to 70 micrometers. In a preferred embodiment, each polyurethane film has a thickness of approximately 35 micrometers.

The films are laid side-by-side together and are placed between oppositely arranged faces of a heat-sealing machine (not shown). The heat-sealing machine is used to make a temporary bag 14 from the films by pressing the films together momentarily. While the films are pressed together, a sufficient amount of heat is applied for a sufficient duration to cause the films to be temporarily melted or adhered together. In a preferred embodiment, the faces of the heat-sealing machine are configured to press the films together along a discrete portion of the films to form a sealed band 16. The band 16 has a parameter that is an approximate outline of the breast enhancer. Alternatively, rather than forming a discrete band, the surfaces of the films can be sealed together except for adjacent centrally positioned surfaces that are used to form the bag. In such an embodiment, the bag rather than a band is an approximate outline of the breast enhancer.

In a preferred embodiment, where the above-described thin films of polyurethane are used to form the breast enhancer, the heat-sealing machine is operated at a temperature of below 120° C., preferably in the range of from about 80° to 115° C., and more preferably at about approximately 95° C. The heat-sealing machine is pressed into contact with discrete portions of the film surfaces at a contact pressure in the range of from about 30 to 50 psi, preferably at approximately 40 psi, for a duration in the range of from about 5 to 15 seconds, and preferably approximately 10 seconds. Using a contact pressure within this range enables the formation of both a temporary and air-bubble free seal. Entrapped air within the sealed band is not desired because it causes air bubbles to form in the finally formed breast enhancer.

It is to be understood that the operating conditions for forming the temporary seal may vary depending on such factors as the type and thickness of the thermoplastic sheet, and the area of the heat sealed surface, i.e., the sealed band.

It is important, however, that the temperature, contact pressure, and duration that is used to form the temporary seal be such that the films are only lightly adhered together to facilitate unsealing or opening by subsequent application of heat and pressure.

In a preferred embodiment, to increase the manufacturing rate, it is desired that more than one temporary bag be formed at a time by the heat-sealing machine. Accordingly, the heat-sealing machine includes sealing faces that are configured to form two symmetrically opposite bags at a time. The faces of the heat-sealing machine are designed to form a temporary seal between the films around a substantial parameter of the bag.

It is desired that a portion of the bag parameter be left unsealed to form an inlet channel 18 extending between the films, through the sealed band and to the bag 14. The inlet channel 18 is formed to accommodate introduction of a liquid silicone composition into the bag. In a preferred embodiment, the inlet channel 18 has a channel width in the range of from about 5 to 15 millimeters, and is preferably approximately 10 millimeters.

It is desired that the band have a sealed film width in the range of from about 10 to 40 millimeters. In a preferred embodiment, the band has a sealed film width of approximately 20 millimeters. It is also desired that the temporary bag formed from the sealed films have a diameter in the range of from about 50 to 100 millimeters, depending on the particular size of breast enhancer desired. It is to be understood that such dimensions are provided for purposes of illustration and reference, and are not intended to be limiting. For example, if desired, temporary bags can be formed having a diameter outside of such range depending on the desired size of the breast enhancer and the particular application.

A tube 20 is inserted between the films, through the inlet channel 18 and into the top portion of the bag 14. The tube 20 has a length sufficient to extend from the top portion of the bag to a position a distance away from the edges of the films to facilitate filling from outside of the bag. It is desired that the tube 20 be formed from a flexible material such as low-density polyethylene and the like. In a preferred embodiment, the tube has an inside diameter of approximately 4.3 millimeters, and has an outside diameter of approximately 6.4 millimeters.

The films 10 and 12, the temporarily sealed bags 14, and the tubes 20 are placed within a rectangular holding frame assembly 22, where the films and bags are placed between a pair of ridged first and second frame members 24 and 26. The films are arranged within the frame assembly 22 so that the bags 14 are centrally positioned therein. The tubes 20 are arranged to extend between top portions of the frame members. The first frame member 24 includes a film-facing surface 28 having a rubber gasket 30 attached thereto. The rubber gasket 30 may be made from silicone rubber and the like and is used to compressively engage the film surface to trap or secure the films within the frame apparatus. The thermoplastic films 10 and 12 are interposed between the rubber gasket 30 and an adjacent surface of the second frame member 26 and the frame members are brought together by clamps (not shown) to firmly secure the films, bags and tubes therebetween. If needed, the edges of the films can be pulled or otherwise arranged to remove surface wrinkles on the films after the frame is clamped together.

The holding frame assembly 22 is turned upright so that the tubes 20 that pass between top portions of the frame members 24 and 26 extend upwardly away from the frame assembly. A liquid silicone composition 32 is introduced into the temporary bags 14 via the tubes 20. A desired silicone composition comprising a heat curable mixture of silicone resins, silicone oils, crosslinking agents, inhibitors, catalysts, and pigments is prepared according to a predetermined formula. It is desired that the resultant composition have a heat curing rate and undergo a degree of cross linking reaction during a curing process to provide a molded product that is neither too soft nor too hard but, rather, possesses a "natural" feel.

A predetermined volume of the liquid silicone composition 32 is measured and is introduced into each temporary bag. The exact amount of liquid silicone composition that is used to fill each temporary bag depends on the particular size of the desired breast enhancer. In an preferred embodiment, where each bag has a diameter as described above, in the range of from about 90 to 200 milliliters of the liquid silicone composition is used to fill each bag. It is to be understood, however, that the exact quantity of liquid silicone composition that is used to fill each bag may outside of the range provided, depending on particular size and application of the breast enhancer.

Figure 2:
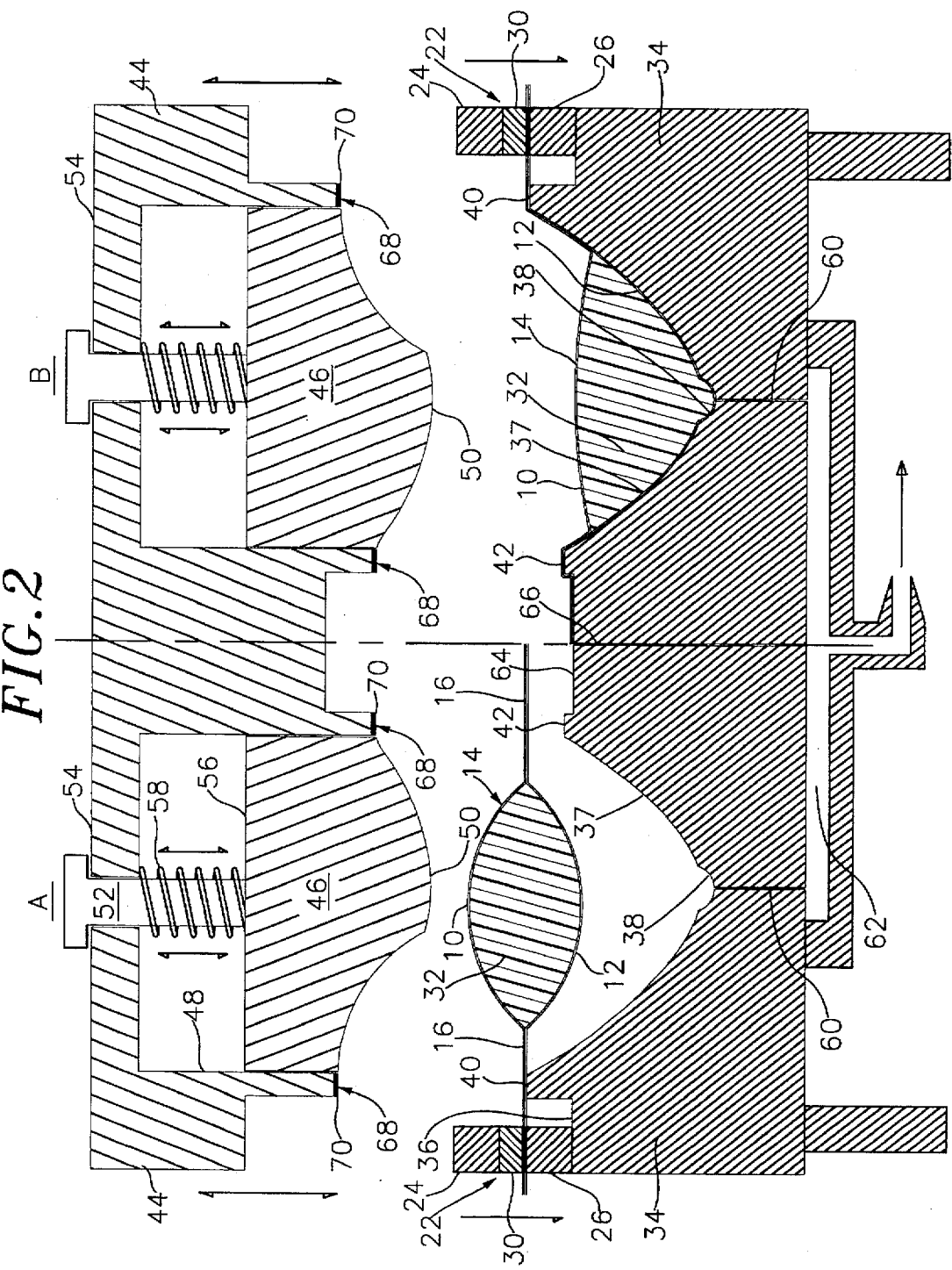
FIG. 2, Sections A and B, are split semi-schematic cross sectional views of a top mold, a floating member, and a bottom mold used to manufacture a breast enhancer according to principles of this invention, illustrating placement of the liquid silicone composition filled bags therebetween both before and after a vacuum is applied to the bottom mold.

Filling each temporary bag with the liquid silicone composition causes each side of the bag to extend or bulge symmetrically outward in opposite directions from the plane of the sheet, as shown in FIG. 2, Section A. After the desired volume of the liquid silicone composition is introduced into each temporary bag, any air bubbles visible by placing a light source behind the bags are bled out of the bags and the tubes are removed. The rubber gasket 30 along the film-facing surface of the first frame member 24 expands after the tubes 20 are removed to seal off the inlet channel 18 to prevent the liquid silicone composition from escaping. If needed, the edges of the films 10 and 12 can be pulled or arranged again to remove any surface wrinkles on the films.

Referring to FIG. 2, Section A, the holding frame assembly 22, containing the bubble-free filled temporary bags, is brought and lowered onto a bottom or female mold 34. The bottom mold 34 includes a recessed portion 36 along its opposed outside edges that is configured to accommodate placement of either the first or second frame member of the holding frame assembly therein. When the holding frame apparatus 22 is placed into the recessed portion 36, the films 10 and 12 and filled temporary bag 14 are suspended above a concave mold surface 37 of the bottom mold 34. In a preferred embodiment, where two bags are formed and filled with liquid silicone composition at a time, the bottom mold comprises two symmetrically opposed concave mold surfaces placed side-by-side together. The concave mold surface 37 includes recessed portion 38 that is used to form a nipple portion of the breast enhancer.

The bottom mold includes a raised lip or rim 40 that is positioned concentrically around an outside edge of the concave surface 37. In a preferred embodiment, the rim 40 has a width in the range of from about 3 to 10 millimeters, and preferably approximately 5 millimeters. The films are placed onto the bottom mold so that the sealed band 16 rests on the rim 40. It is desired that the sealed band 16 have an inside diameter that is smaller than an inside diameter of the rim 40 so that the volume of liquid silicone composition encased within the bag be disposed completely within the concave mold surface 37. Placement of the sealed band inside diameter completely within the concave mold surface ensures that the liquid silicone composition will not migrate past the rim, after the top and bottom molds are compressively engaged together and the temporary seal is opened, to interfere with the formation of a weld between the films 10 and 12, as described below. In a preferred embodiment, it is desired that the sealed band have an inside diameter that extends at least 5 millimeters away from the rim 40 within the concave mold surface, and preferably approximately 10 millimeters away from the rim 40 within the concave mold surface.

It is also desired that the sealed band 16 have an outside diameter that is larger than an outside diameter of the rim 40 to ensure that no air pockets exist or can be formed between the films 10 and 12 within the concave mold surface. In a preferred embodiment, it is desired that the sealed band have an outside diameter that extends away from an outside edge of the rim at least 5 millimeters, and preferably approximately 10 millimeters away from the outside edge of the rim.

The raised rim 40 includes a recessed section 42 that is positioned below the films and does not contact the films when they are initially placed over the bottom mold. In a preferred embodiment, where two temporary silicone filled bags are formed, the recessed section 42 is positioned between the two concave mold surface 37.

A top or male mold 44 is disposed above the bottom mold 34 and is vertically movable relative to the bottom mold. The top mold includes a floating mold member 46 that is slidably positioned within a housing 48 in the top mold. In a preferred embodiment, where two temporary bags are formed, the top mold 44 includes two floating mold members 46 positioned to correspond with respective concave mold surfaces of the bottom mold. Each floating mold member includes a convex external surface 50. Each floating mold member 46 is retained within a respective housing 48 by a bolt 52 that extends through a back side surface 54 of the top mold 44 and is attached to a back side surface 56 of the floating mold. A spring 58 is disposed around the bolt 52 to exert an outwardly directed force onto the floating member and to provide a desired degree of resistance to the floating member being retracted into the housing. In a preferred embodiment, the spring has a compression rate of approximately 33 lbs/in.

A vacuum is applied to the bottom mold by an external vacuum source (not shown). The vacuum is directed to the concave mold surface 37 via vacuum channels 60 and 62, and is directed to a the recessed section 42 of the bottom mold via vacuum channel 66. The vacuum acts to draw the films 10 and 12, and the liquid silicone composition filled bags, into the bottom mold and against respective adjacent bottom mold surfaces, as illustrated in FIG. 2, Section B. Applying a desired amount of vacuum causes each liquid silicone filled bag to completely fill and take on the shape of the concave mold surface 37, including the recessed portion 38 that forms the nipple portion of the breast enhancer.

Figure 3:
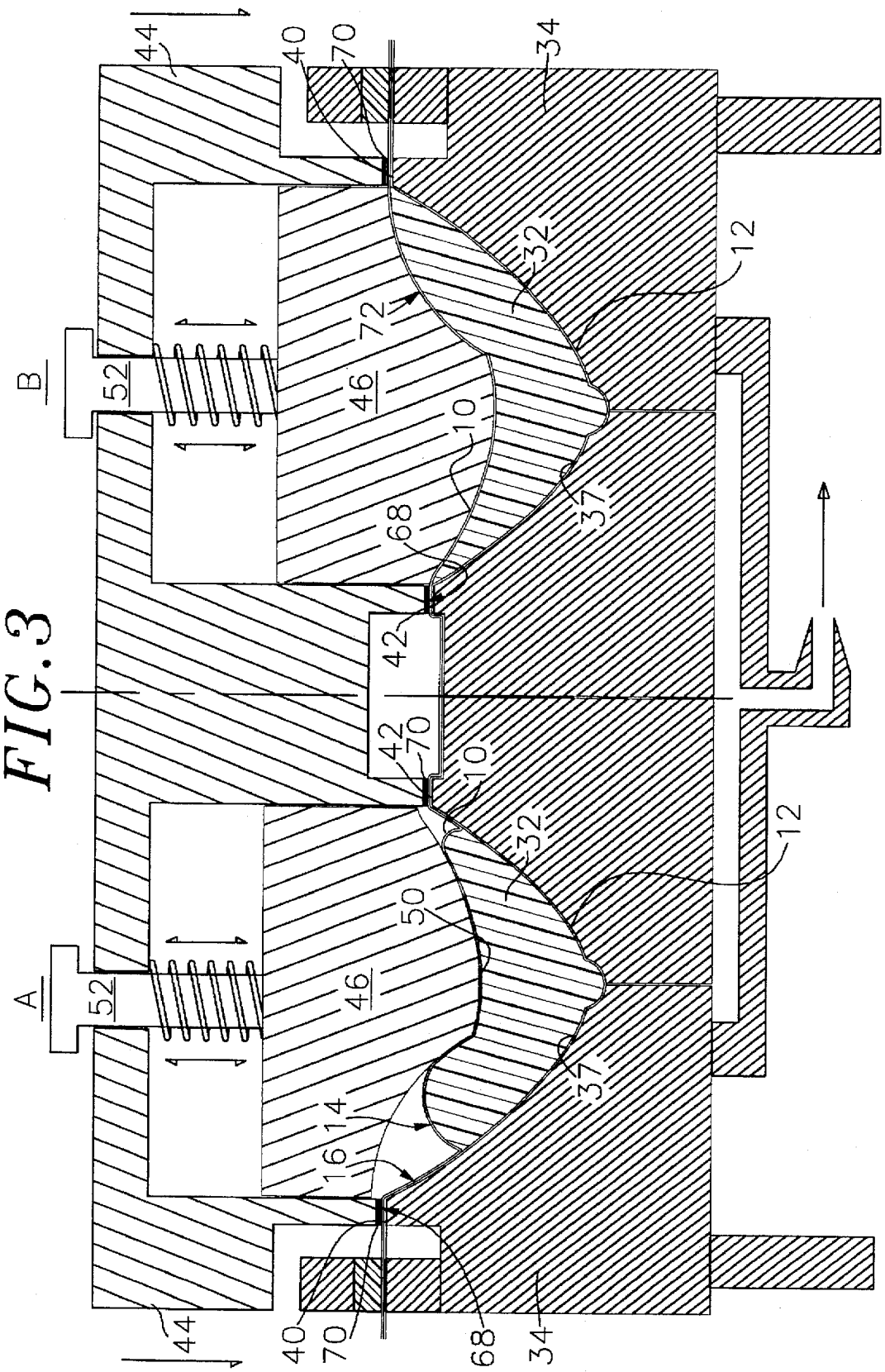
FIG. 3, Sections A and B, are split semi-schematic cross sectional views of the top mold and the floating member lowered onto the bottom mold and encasing the liquid silicone composition filled bags, illustrating placement of the floating member before and after the temporary seal between the thermoplastic films are unsealed or opened.

Referring to FIG. 3, Sections A and B, the top mold 44 is lowered onto the bottom mold 34 so that a raised rim or lip 68, that extends outwardly away from the top mold surface, is placed adjacent corresponding rim portions 40 and 42 of the bottom mold 34 to trap bands of the films 10 and 12 that extend around each liquid silicone filled bag therebetween. In a preferred embodiment, the rim 68 has a width in the range of from about 3 to 10 millimeters, and preferably 5 millimeters. The raised rim 68 of the top mold includes a sealing surface 70 that is formed from temperature resistant silicone rubber, Viton rubber, and the like. The silicone rubber sealing surface 70 is of sufficient thickness to provide a desired degree of thermal conduction therethrough to form a permanent seal between the films 10 and 12 during further processing. As the rim portions of each top and bottom mold are placed into contact with one another, the floating mold member 46 is lowered into the concave mold surface 37 so that the convex external surface 50 of the floating member presses against an adjacent surface of the liquid silicone filled bag 14, as shown in FIG. 3, Section A.

The amount of pressure that is applied to the liquid silicone filled bag 14 by the floating mold member 46 is dependent on the size and spring rate of the spring 58 that is used to apply an outwardly directed force on each floating mold member. It is desired that the spring 58 be designed to permit the floating member to retract a distance into the housing upon contact with and compression of the bag, and not over compress the bag. It is desired that the bag not be over compressed to avoid possible bag rupture or premature opening of the temporary seal.

The top and bottom molds are compressively engaged together by application of an external force provided by conventional push and pull type means such as a hydraulic or pneumatic cylinder. In a preferred method, it is desired that the push and pull means comprise a pneumatic cylinder capable of accommodating in the range of from about 80 to 150 psig of air pressure. In a preferred embodiment, a sufficient external force is used to provide a pressure of approximately 250 psi along the sealing surface and rims of the top and bottom molds. The vacuum is removed from the bottom mold once the top and bottom molds are compressively engaged together. At least one of the floating member and the bottom mold is heated to a sufficient temperature for a sufficient amount of time to open the temporary seal.

The melting point of the polyurethane material used to form the first and second films 10 and 12 is in the order of 180° to 210° C. It is, therefore, desired that the molds be heated to a temperature below the film melting point. In a preferred embodiment, the top mold, the floating member, and the bottom mold are each heated by electrical heating means to a temperature in the range of from 115° to 150° C. for a period of about 10 to 25 minutes. Preferably, the top mold is heated to a temperature of approximately 150° C., the floating member is heated to a temperature of approximately 115° C., and the bottom mold is heated to a temperature of approximately 120° C. It is understood that the heating temperature of the molds and the duration of the heating operation may vary, as both are dependent on such factors as the type and thickness of films that are used to form the temporary bags, and the type and volume of liquid silicone composition that is used to fill the temporary bag.

In a preferred embodiment, the floating member and bottom mold are each heated to cause the temporary adhesion seal 16 between the films to soften, and pressure is applied to the filled bag to cause the liquid silicone composition contained within the bag to push against the softened temporary seal and open the seal. Opening the temporary seal causes the liquid silicone composition to squeeze into the open volume or cavities existing within the films and between the concave and convex mold surface to completely fill the mold cavity, as shown in FIG. 3, Section B. In a preferred embodiment, where the floating mold member and bottom mold are each operated within the temperature range described above, the temporary seal is softened and opened after about two minutes.

As the temporary seal is opened, the compression force exerted by the floating member onto the filled bag causes the liquid silicone composition to migrate and fill previously unoccupied portions of the mold cavity. As the liquid composition migrates into the mold cavity, the floating member travels further toward the bottom mold. In a preferred embodiment, the amount of liquid silicone composition that is used to fill the temporary bag is selected so that after the temporary seal is opened, the floating mold member 46 is allowed to extend outwardly from the housing a distance governed by the bolt 52. The bolt can be screwed in and out of the floating mold member to adjust the maximum travel of the floating mold member into the concave mold surface.

Application of heat to the top and bottom mold, after the temporary seal has been opened, welds together the portions of the films sandwiched between the top and bottom molds to entrap the liquid silicone composition therein. Further application of heat to the floating mold member and bottom mold acts to cure the silicone composition to form a silicone gel. The volume of silicone gel is encased between the welded together films to form the breast enhancer 72. Since both the particular formula of the liquid silicone composition, i.e., proportions and compositions of silicone oils, resins, inhibitors, catalyzers and the like, and the volume of the liquid silicone composition dictates the cure rate of the composition, it is to be understood that the amount of time that the heaters are operated can vary. It is also to be understood that the heating temperature may be varied to achieve a desired degree of control over the cure rate of the liquid silicone composition, which again is dependent on the particular formula and volume of the liquid silicone composition. During the cure process, the floating mold member 46 is allowed to move as required to accommodate any volume changes.

After the liquid silicone composition has been cured and the first and second films welded together, the heaters are turned off and the top mold, floating member, and bottom mold are cooled to a predetermined temperature. In a preferred method, the top mold, floating member, and bottom mold are water cooled to a temperature of approximately 50° C. for a period of approximately two minutes. The top mold is retracted away from the bottom mold by reversing the action of the pneumatic cylinder and the breast enhancer 72 and frame assembly 22 are removed from the concave mold surface 37 of the bottom mold, as shown in FIG. 4, Section A. A next breast enhancer is manufactured by repeating the above-described sequence of process steps. The molds are cooled to so that the film of the next filled bag and frame assembly loaded within the bottom mold, that is placed adjacent the concave mold surface, does not become softened and rupture when the vacuum is applied to the concave mold surface.

After the breast enhancer 72 is removed from the bottom mold, the welded together edges of the first and second polyurethane films are trimmed of any unwanted excess portions (as shown in FIG. 4, Section B) and the breast enhancer is ready for packaging and shipping. The trimming process can be performed by hand using conventional cutting means such as scissors and the like, or can be performed by using a trimming machine in the form of a die cutter and the like. In a preferred method, before final trimming the breast enhancer is further air cooled to a hand-touchable temperature.

The method of making a breast enhancer as described above and as illustrated has several advantages over known methods for making artificial breasts and breast prostheses in that such method does not involve a multitude of complicated steps associated with forming a temporary bag, filling the bag with liquid silicone composition, loading the filled bag into the mold, opening the temporary seal, and forming a permanent seal around the parameter of the breast enhancer and curing the silicone composition. Additionally, the step of forming a bag using a temporary seal which can be opened upon heating allows for one size of bag to be used for different sizes of breast enhancer. For example, a bag formed for use in a large breast enhancer would have the same temporary sealed band diameter as that used for forming a smaller breast enhancer. However, such bag would be filled with a greater volume of liquid silicone composition to migrate and fill the complete mold cavity during the heating process. Because of the great elasticity of the polyurethane film, one bag can accommodate a wide range of volumes of the liquid silicone composition.

Additionally, the use of this method requires little operator intervention since specialized removable inserts and the like are not used in conjunction with the female mold to effect formation of the nipple portion. Accordingly, the use of the method of this invention produces a breast enhancer in a manner that is both more efficient and economically desirable than other known methods. Another advantage of this improved method is that it allows for premaking of temporary bags so than an operator can maximize press efficiency and minimize press time by replacing a frame assembly containing a just-formed breast enhancer with a frame assembly containing a liquid silicone composition filled bag.

Although a specific method for making a breast enhancer has been described and illustrated herein according to principles of this invention, many modifications and variations will be apparent to those skilled in the art without departing from the spirit thereof. For example, instead of raising and lowering the top mold, the bottom mold could be moved against a stationary top mold. Other parts or steps may also be reversed, for example, the sealing surface and lip. The top mold may be mounted on a hinge and swing upwardly and to one side instead of moving entirely vertically. Also, the bottom mold can be configured having a convex mold surface and the floating mold member can be configured having a concave mold surface. Additionally, instead of making only one or two breast enhancers at a time, the top mold, floating member, and bottom mold can be modified to allow making various different numbers of breast enhancers at a time.

Thus, while a preferred method has been described, it should be understood that within the scope of the appended claims, the invention may be practiced otherwise than as specifically illustrated and described.

What is claimed is:

1. A method for making a breast enhancer comprising the steps of:

forming a temporary adhesion seal between two films of thermoplastic material to form a temporary bag between the films;

introducing a liquid silicone composition into the temporary bag to form a liquid silicone composition filled bag;

placing the liquid silicone composition filled bag between complementary mold members;

bringing the mold members together to compress the liquid silicone composition filled bag, thereby causing the temporary adhesion seal to be broken by the liquid silicone composition and causing the liquid silicone composition to pass between the two films;

compressively engaging the two films by opposed surfaces of the complementary mold members to weld together the two films of thermoplastic material and form a sealed bag of liquid silicone composition;

curing the liquid silicone composition to form a sealed bag of cured silicone composition; and removing the sealed bag of cured silicone composition from the complementary mold members.

2. A method as recited in claim 1 comprising, during the step of forming a temporary adhesion seal, leaving a portion of the two films of thermoplastic material unsealed, forming an inlet channel between the two films that extends into the temporary bag.

3. A method as recited in claim 2 comprising, before the step of introducing the liquid silicone composition, placing the temporary bag within a holding frame apparatus.

4. A method as recited in claim 3 comprising, before the step of placing the temporary bag within the holding frame apparatus, inserting a tube into the inlet channel to facilitate introduction of the liquid silicone composition into the temporary bag.

5. A method as recited in claim 4 comprising removing the tube before the step of bringing the mold members together.

6. A method as recited in claim 2 where during the step of forming a temporary adhesion seal, a sealed band is formed between the films that defines a perimeter boundary of the temporary bag.

7. A method as recited in claim 1 comprising, before the step of bringing the mold members together:
placing the filled bag over a concave surface of a bottom mold member and over a rim positioned concentrically around an outside portion of the concave surface; and
applying a vacuum to the bottom mold to cause the filled bag to be drawn against the bottom mold, whereby a surface of the filled bag is drawn against the concave surface of the bottom mold member.

8. A method as recited in claim 7 comprising placing the filled bag over the concave surface to that at least a portion of the temporary adhesion seal is adjacent the concave surface.

9. A method as recited in claim 1 comprising heating the filled bag during the step of bring the mold members together.

10. A method as recited in claim 1 further comprising heating the complementary mold members during the steps of welding and curing.

11. A method for making a breast enhancer comprising the steps of:
forming a temporary adhesion seal between two adjacent films of thermoplastic material, the temporary adhesion seal defining a perimeter boundary of a temporary bag formed therebetween;
introducing a volume of liquid silicone composition into the temporary bag to form a liquid silicone composition filled bag;
placing the liquid silicone composition filled bag between complementary and opposed surfaces of first and second molds;
bringing the first and second molds together to contact and encase the liquid silicone composition filled bag between respective mold surfaces;
compressing the liquid silicone composition within the liquid silicone composition filled bag to release the temporary adhesion seal and allow the liquid silicone composition to migrate between the adjacent films and respective mold surfaces;
compressively engaging the complementary and opposed surfaces of the first and second molds to weld together portions of the films to encase the liquid silicone composition therein and form a sealed bag of liquid silicone composition;
curing the liquid silicone composition within the liquid silicone composition sealed bag to form the breast enhancer; and
removing the breast enhancer from the first and second molds.

12. A method as recited in claim 11 wherein during the step of forming a temporary adhesion seal, a band of sealed together film is formed that has an inside perimeter dimension that is less than a mold cavity formed between complementary surfaces of the first and second molds.

13. A method as recited in claim 12 wherein the band has an outside perimeter dimension that is greater than the mold cavity.

14. A method as recited in claim 13 wherein during the step of welding, a portion of the films between the inside and outside perimeter dimension of the band are welded together.

15. A method as recited in claim 11 wherein during the step of placing, the liquid silicone composition filled bag is placed adjacent a concave surface of the first mold, wherein at least a portion of the temporary adhesion seal is positioned adjacent the concave surface and a remaining portion of the temporary adhesion seal is positioned adjacent a rim portion of the first mold that surrounds the concave surface.

16. A method as recited in claim 15 wherein during the step of placing, the remaining portion of the temporary adhesion seal is positioned adjacent a sealing surface positioned along a surface of the second mold that corresponds to the rim portion of the first mold.

17. A method as recited in claim 16 wherein during the step of compressively engaging, the remaining portion of the temporary adhesion seal is sandwiched between the rim portion of the first mold and the sealing surface of the second mold, and the rim portion and sealing surface are heated to a temperature sufficient to weld together portions of the film.

18. A method as recited in claim 16 wherein during the step of placing, the liquid silicone composition filled bag is placed adjacent a movable member of the second mold that has a convex mold surface, the movable member being adapted to exert a sufficient force against the liquid silicone composition filled bag to compress the liquid silicone and thereby cause release of the temporary adhesion seal.

19. A method as recited in claim 18 comprising, during the steps of compressively engaging and curing, heating at least one of the movable member or the first mold.

20. A method as recited in claim 11 comprising, during the step of forming the temporary adhesion seal, leaving a portion of the two films of thermoplastic material unsealed, forming an inlet channel between the films that extends into the temporary bag to permit introduction of the liquid silicone composition therein.

21. A method as recited in claim 11 comprising, before the step of introducing liquid silicone composition, placing the temporary bag into a holding frame apparatus.

22. A method for making a breast enhancer comprising the steps of:
forming a temporary adhesion seal between two adjacent films of thermoplastic material, wherein the temporary adhesion seal forms a band that defines a perimeter of a temporary bag formed therebetween, and wherein the temporary bag includes an inlet channel that extends through the band and into the temporary bag;
introducing a volume of liquid silicone composition through the inlet channel into the temporary bag to form a liquid silicone composition filled bag;
placing the liquid silicone composition filled bag between a top mold and a bottom mold;
bringing the top and bottom molds together to encase the filled bag and at least a portion of the band within a mold cavity formed between complementary top and bottom mold surfaces;

compressing the liquid silicone composition filled bag to cause the liquid silicone composition contained therein to exert a force against the temporary adhesion seal to release the temporary adhesion seal and allow the liquid silicone composition to migrate between the two adjacent films and fill the mold cavity;

welding together portions of the films that are positioned outside of the mold cavity to encase the liquid silicone composition therebetween and formed a sealed liquid silicone composition bag;

curing the liquid silicone composition to form the breast enhancer; and removing the breast enhancer from the top and bottom molds.

23. A method as recited in claim 22 wherein during the step of forming a temporary adhesion seal, the band that is formed has an inside perimeter dimension that is smaller than a diameter of the mold cavity, and has an outside perimeter diameter that is greater than the diameter of the mold cavity.

24. A method as recited in claim 23 wherein during the step of forming a temporary adhesion seal, the band that is formed has an inside perimeter dimension that is at least 5 millimeters smaller than the diameter of the mold cavity, and has an outside perimeter diameter that is at least 5 millimeters greater than the diameter of the mold cavity.

25. A method as recited in claim 22 wherein during the step of placing the liquid silicone composition filled bag, the liquid silicone composition filled bag is placed between a floating member of the top mold and the bottom mold, and wherein during the step of compressively engaging, the floating member is adapted to impose a compressive force against the liquid silicone composition filled bag.

26. A method as recited in claim 25 wherein during the steps of welding and curing, at least one of the floating member, top mold, or bottom mold are heated to a temperature in a range of from 115° to 150° C.

27. A method for making a breast enhancer comprising the steps of:

forming a temporary adhesion seal between two films of thermoplastic material to form a sealed band, the sealed band defining a perimeter of a temporary bag formed therebetween, wherein the sealed band includes an inlet channel that passes between the films and into the temporary bag;

introducing a tube into the inlet channel;

placing the temporary bag into a holding frame apparatus;

introducing a volume of liquid silicone composition through the tube in the inlet channel and into the temporary bag to form a liquid silicone composition filled bag;

removing the tube from the inlet channel;

placing the holding frame apparatus and the liquid silicone composition filled bag between a top mold and a bottom mold;

bringing the top and bottom molds together to encase the liquid silicone composition filled bag within a mold cavity formed between a floating member of the top mold and the bottom mold, whereby an imposed compression force on the liquid silicone composition filled bag causes the temporary adhesion seal to release so that the liquid silicone composition migrates between the films and fills the mold cavity, wherein at least a portion of the sealed band is disposed within the mold cavity;

welding portions of the films together outside of the mold cavity to encase the liquid silicone composition therein to form a liquid silicone composition sealed bag;

curing the liquid silicone composition to form a silicone gel sealed bag; and removing the silicone sealed bag from the mold cavity.

28. A method as recited in claim 27 wherein during the steps of welding and curing, at least one of the floating member, top mold, or bottom mold are heated to a temperature in a range of from 115° to 150° C.

* * * * *